United States Patent [19]

Lampotang et al.

[11] Patent Number: 5,391,081
[45] Date of Patent: Feb. 21, 1995

[54] METHOD AND APPARATUS FOR SIMULATING NEUROMUSCULAR STIMULATION DURING MEDICAL SURGERY

[75] Inventors: Samsun Lampotang; Michael S. Good; Joachim S. Gravenstein; Ronald G. Carovano, all of Gainesville, Fla.

[73] Assignee: University of Florida Research Foundation, Incorporated, Gainesville, Fla.

[21] Appl. No.: 882,467

[22] Filed: May 13, 1992

[51] Int. Cl.$^6$ .............................................. G09B 23/28
[52] U.S. Cl. ..................................... 434/262; 434/265; 434/267
[58] Field of Search ............... 434/262, 272, 275, 265, 434/267, 266, 268, 366; 128/28, 741, 782, 419 R, 421, 422; 364/413.03, 413.27, 413.02, 413.04; 395/920, 924; 623/25; 607/48, 54, 56, 120

[56] References Cited

U.S. PATENT DOCUMENTS

| | | | |
|---|---|---|---|
| 3,520,071 | 7/1970 | Abrahamson et al. | 35/17 |
| 4,561,851 | 12/1985 | Ferreira et al. | 434/272 |
| 4,570,640 | 2/1986 | Barsa | 128/741 |
| 4,878,388 | 11/1989 | Loughlin et al. | 73/866 |
| 4,907,973 | 3/1990 | Hon | 434/262 |
| 4,964,804 | 10/1990 | Carr et al. | 434/366 X |
| 4,996,980 | 3/1991 | Frankenberger et al. | 128/200 |

FOREIGN PATENT DOCUMENTS

0612259 5/1978 U.S.S.R. .......................... 364/413.03

OTHER PUBLICATIONS

Michael L. Good et al., "Anesthesia Simulators and Training Devices," *International Anesthesiology Clinics*, 27(3):161–166 (Fall 1989).

Michael L. Good et al., "Hybrid Lung Model for Use in Anesthesia Research and Education," *Anesthesiology*, Abstract No. A982, 71(3) (Sep. 1989).

David M. Gaba et al., "A Comprehensive Anesthesia Simulation Environment: Re-creating the Operating Room for Research And Training," *Anesthesiology*, 69:387–394 (1988).

Michael L. Good et al., "Critical Events Simulation for Training in Anesthesiology," *Journal of Clinical Monitoring*, 4(2):140 (Apr. 1988).

Samsun Lampotang et al., "A Lung Model of Carbon Dioxide Concentrations with Mechanical or Spontaneous Ventilation," *Critical Care Medicine*, 14(12):1055–1057 (1986).

Stephen Abrahamson, "Human Simulation for Training in Anesthesiology," *Medical Engineering in Anesthesiology*, pp. 370–374 (1974).

J. S. Denson et al., "A Computer-Controlled Patient Simulator," *Jama*, 208(3):504–508 (Apr. 21, 1969).

*Primary Examiner*—Richard J. Apley
*Assistant Examiner*—John P. Leubecker

[57] ABSTRACT

A method and associated apparatus for simulating neuromuscular stimulation in real time during simulated medical surgery using a manikin, such as ulnar nerve stimulation to detect the degree of neuromuscular blockade and external stimulation of nerves to produce evoked potentials so as to monitor the integrity of nerves during surgery is provided. Such simulation allows for the active participation of trainees with the simulation apparatus to experience real world medical procedures in a setting that closely mimics the real world.

23 Claims, 5 Drawing Sheets

METHOD AND APPARATUS FOR SIMULATING NEUROMUSCULAR STIMULATION DURING MEDICAL SURGERY

BACKGROUND OF THE INVENTION

This invention relates to a medical simulator for modeling neuromuscular stimulation during surgery that is especially useful for training personnel in the medical and related arts or for demonstration or testing of medical apparatus used in conjunction with neuromuscular stimulation. More particularly, the invention relates to a method and associated apparatus for simulating neuromuscular stimulation in real time, such as ulnar nerve stimulation to detect the degree of neuromuscular blockade and the external stimulation of nerves to produce evoked potentials so as to monitor the integrity of nerves during surgery. Such simulation allows for the active participation of trainees with the simulation apparatus to experience real world medical procedures in a setting that closely mimics the real world.

The concepts involved in simulation of complex procedures are well established in the aviation and military arts. Simulation in the medical context is not so well developed. Various computer-controlled anesthesiological training simulators, such as those described in U.S. Pat. No. 3,520,071; D. M. Gaba et al., *Anesthesiology*, 69:387 (1988); M. L. Good, *Int. Anesthesiology Clinics*, 27(3):161 (1989); and U.S. Pat. No. 4,996,980, are known in the art. Further, lung simulators, such as those described in S. Lampotang, *Crit. Care Med.*, 14(12):1055 (1986); M. L. Good, *Anesthesiology*, Abstract No. A982, 71:(3A) (1989); and U.S. Pat. No. 4,878,388 and other medical simulators, such as the simulator described in U.S. Pat. No. 4,907,973, which utilizes a video display of simulated internal conditions to model invasive or semi-invasive procedures, are known.

However, none of these disclosures addresses the simulation of neuromuscular stimulation, particularly the electrical stimulation of the ulnar nerve during anesthetized medical procedures or the electrical, auditory or visual external stimulation to produce evoked potentials. Because the results of neuromuscular stimulation can be difficult to interpret and because other factors, such as amount and kind of anesthetics, equipment malfunction or even the patient's temperature, can affect these results, there exists a need for a simulator capable of modeling neuromuscular stimulation. Further, there exists a need for a method to train medical personnel, particularly novice medical personnel, to use neuromuscular stimulation equipment of ever-increasing complexity and cost without putting the patient at risk of injury.

Throughout this application, various publications are referenced. The disclosures of these publications in their entireties are hereby incorporated by reference into this application in order to more fully describe the state of the art to which this invention pertains.

SUMMARY OF THE INVENTION

This invention relates to an apparatus and method for simulating neuromuscular stimulation during surgery, particularly a nerve stimulator simulator and an evoked potentials simulator. The simulators of this invention are capable of standing alone or being integrated into a simulator capable of emulating a wide variety of clinical variables, such as an anesthesiological training simulator.

In particular, this invention relates to a method of simulating neuromuscular stimulation in real time during simulated medical surgery using a manikin, comprising the steps of (a) applying at least one pulse corresponding to a nerve stimulation protocol to a pulse sensing means associated with the manikin, wherein the at least one pulse is applied using a nerve stimulator; (b) automatically detecting the at least one pulse and identifying the corresponding nerve stimulation protocol; (c) computing a simulated response to the identified nerve stimulation protocol according to a time- and event-based script, a computer model or a combination of a time- and event-based script and a computer model; and (d) automatically actuating at least one output device associated with the manikin in real time according to the computed simulated response to simulate the neuromuscular stimulation associated with the nerve stimulation protocol. More particularly, this invention relates to simulating ulnar nerve stimulation, spinal cord or peripheral nerve stimulation, cranial nerve stimulation by auditory means and optical nerve stimulation by visual means.

This method can further include the steps of (a) administering a simulated or real neuromuscular blockade drug to the manikin; (b) detecting the time at which the neuromuscular blockade drug is administered, detecting the quantity of neuromuscular blockade drug administered, and detecting the kind of neuromuscular blockade drug administered; and (c) utilizing the time the drug was administered, the quantity of drug administered, and the kind of drug administered in computing a simulated response on the manikin so as to provide a combined simulated response in accordance with both the degree of blockade and the identified nerve stimulation protocol.

Various output devices are provided, including a thumb twitch actuator, which moves a thumb on a hand of the manikin relative to the fingers on the hand a distance, time duration and pattern computed according to the nerve stimulation protocol. Further, the thumb is capable of transmitting a force related to the distance computed according to the nerve stimulation protocol when movement of the thumb is retarded.

DETAILED DESCRIPTION OF THE INVENTION

The invention described herein relates to a method and apparatus for simulating neuromuscular stimulation during medical surgery, particularly the use of a nerve stimulator simulator and an evoked potentials simulator. The following first discusses the most generic simulation engine that will address the specific needs of medical simulation. Further, two specific embodiments, the nerve stimulator (NS) or twitch simulator and an evoked potentials (EP) simulator, are described followed by a discussion of the distributed processing network, which is used to support the simulator of the present invention and is an important component of the implementation.

Generic Medical Simulation Concepts

From an engineering viewpoint, the purpose of medical simulation is to create a clinically realistic and accurate, dynamic environment where clinical variables (SpO2, blood pressure, cardiac output, evoked potentials, skin temperature, urine output, end-tidal gas concentrations, etc.) change with time in a clinically credible fashion. For clinical accuracy, the dynamic changes in the clinical variables controlled by the simulation engine must be context sensitive and synchronized to the sequence and flow of events in the simulated domain.

Figure 1:
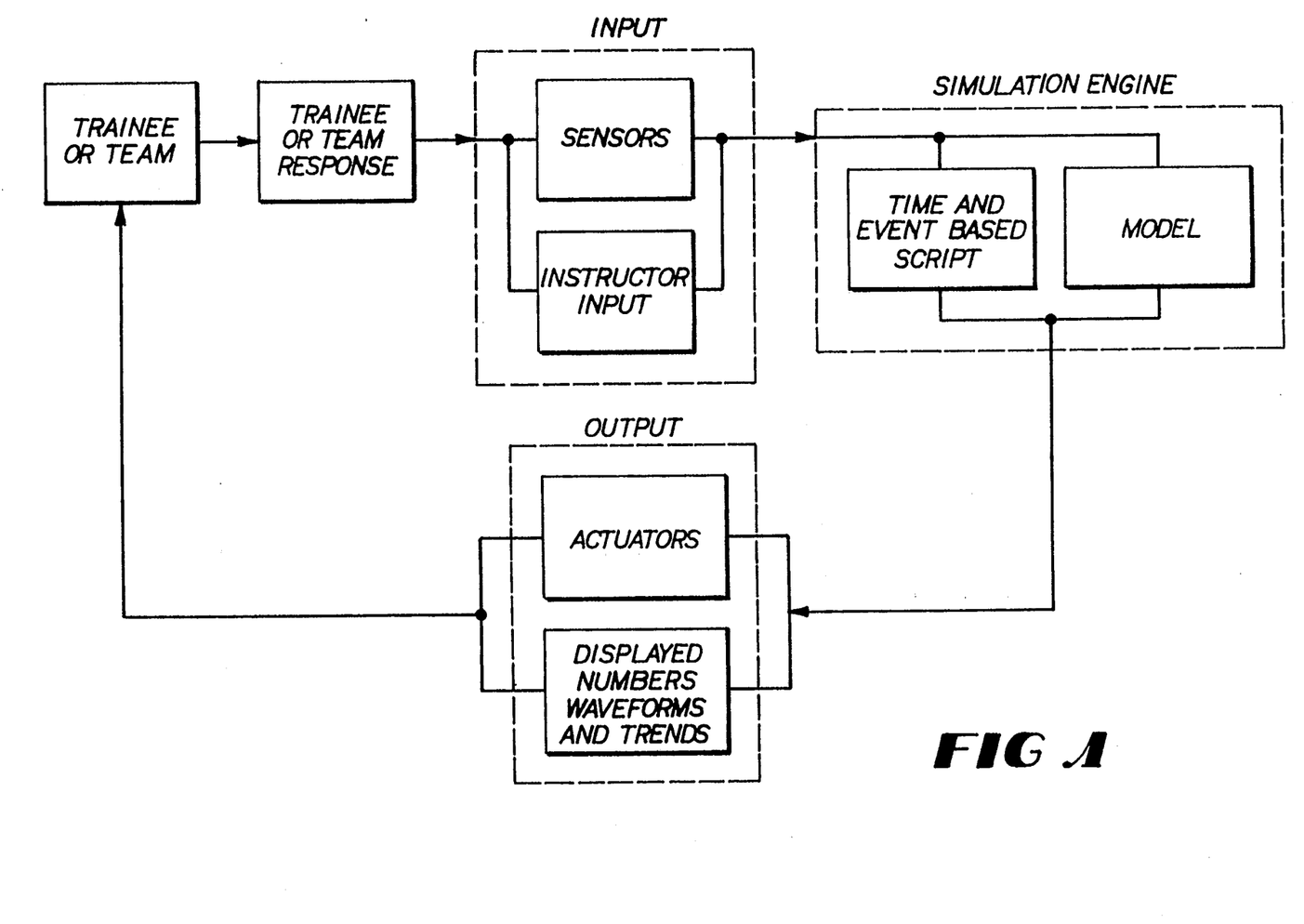
FIG. 1 shows a block diagram generic representation of the processes involved in medical simulation.

Furthermore, the actions of the trainee must be sensed so that the simulation engine can be informed-of the trainee's responses and, in real time, generate appropriate changes in the variables that would normally result from the trainee's reactions. Thus, the process of simulation can be divided into three logical sections: input, simulation engine and output. This functional division is illustrated in FIG. 1.

Input can be from any device that can be interfaced to the computer(s) that run the simulation engine. Some examples are (a) standard I/O devices for computers like a mouse, trackball, touchscreen, light pen or keyboard; (b) custom devices like proximity switches, potentiometers, pressure and flowrate transducers, optical emitter-detector pairs, magnetic switches; and (c) the standard equipment used in a normal OR or medical environment like gas analyzers, ventilators, and blood pressure monitors. To use the equipment and monitors in an OR as input devices, communication between the device and the simulation engine computer must be established. This is usually accomplished via the analog or serial port that is usually available on medical electronic equipment but is not restricted to that modality. Obviously, the list of input devices above is but a small sample of the mechanisms that can be used.

The engine that runs the simulation can be either a time and event-based script or a mathematical model, both running on a computer. The time and event-based script has the advantage that it is readily implemented and requires less program memory compared to the mathematical model, which usually requires a significant investment in time and effort for development and validation. However, the mathematical model benefits from more flexibility than the script because the script can only cope with events that are pre-coded in it. The two approaches are not mutually exclusive and can be combined into a hybrid simulation engine. For example, a time-based script will always be necessary to trigger faults at specific points in time in an equipment fault scenario. Or the script can trigger the execution of one or several mathematical models of physiological or kinetic systems.

The simulation engine can thus simulate many different clinical variables, such as cardiac output, blood pressure, pupil size, neuromuscular blockade, evoked potentials, skin and core temperatures, heart rate, ejection fraction, and the like. The simulation engine can also introduce artifacts peculiar to the clinical variable being monitored, such as motion artifact on an SpO2 plethysmogram, bradycardic diastolic hypotension and electrical interference on an electrocardiogram. Furthermore, the simulation engine can simulate changes in one variable resulting from a change in another variable that would actually be observed in a real clinical setting. For example, the disturbance of evoked potentials by volatile anesthetics can be portrayed when anesthesia begins at the start of a simulated surgical procedure.

The output devices can be any actuator, display device or monitoring instrument that can be interfaced and controlled by a computer and that can provide feedback to the trainee via the five senses (sight, hearing, touch, smell and taste). Among others, the output device can be a fault actuator, such as valves and solenoid-actuated pins that are usually triggered according to a time-based script, or a regular actuator, such as a speaker that produces different heart sounds as instructed by the simulation engine. Other output devices include monitoring instruments, such a pulse oximeter or blood pressure monitor or EP monitor, whose displayed values, waveforms and trends are controlled by the simulation engine. The purpose of the output device is to close the simulation loop and provide feedback to the trainee.

Feedback to the trainee or team being trained can be limited to visual (alarms, cyanosis, displays etc.), auditory (alarms, heart and breath sounds, etc.) and tactile (palpable pulse, etc.) means. However, the output devices can be readily extended to include the other senses of the trainee like smell and taste. For example, a simulated vaporizer leak could be accompanied by volatile anesthetic being actually released in the general region of the vaporizer by a computer controlled syringe or infusion pump.

Twitch Simulator

Neuromuscular blocking agents are used extensively in contemporary anesthesia practice to insure a motionless operating field (e.g., eye surgery, craniotomy) or to facilitate surgical exposure of muscular body cavities (e.g., laparotomy, sternotomy). A neuromuscular blockade monitor, often referred to as a twitch monitor or nerve stimulator (NS), is used by the anesthesiologist for visual and tactile assessment of the degree of neuromuscular blockade (NMB) caused by the neuromuscular blockade drugs, which can be classified as either depolarizing or non-depolarizing.

One embodiment of the present invention, referred to herein as a twitch simulator, simulates the twitch response of a patient's thumb to an electrical stimulus applied at the ulnar nerve. The twitch simulator includes a means for applying at least one electric pulse, preferably by a nerve stimulator, more preferably a commercial nerve stimulator such as Model NS-2C (Professional Instruments) or Myotest (Biometer, Denmark). Typically, the nerve stimulator is capable of generating five main modes of electrically neuromuscular stimulation, referred to herein as nerve stimulation protocols, to the ulnar nerve: single twitch, train of four (TOF), tetanic, post tetanic count (PTC) and double burst (DB). The latter two nerve stimulation protocols are more recently developed and less commonly used in current clinical settings, but apparently are useful clinically as described by J. Viby-Mogensen in "Neuromuscular Monitoring" in *Anesthesia* (3rd ed), vol. 2, (R. D. Miller. ed), Churchill Livingstone, N.Y. (1990). The last mode, double burst stimulation, may not be available on all commercially available twitch monitors (such as Model NS-2C). Thus, as appreciated by one skilled in the art, the term "nerve simulation protocol" can refer to a variety of nerve stimulation patterns, including the train of three pulses detected when the battery for the nerve stimulator is in a low condition. Because teaching state of the art procedures via simulation is desirable, the preferred twitch simulator is capable of generating a variety of nerve stimulation protocols, including PTC and DB stimulation.

TABLE 1

| | |
|---|---|
| Single-twitch stimulation | 0.1 or 1.0 Hz, usually 0.1 Hz pulse duration: 0.25 ms |
| Train of four (TOF) stimulation | 4 pulses spaced 0.5 s apart TOF ratio or fade indicates degree of neuromuscular blockade delivered in single train or repetitively every 10-12 s |
| Tetanic stimulation | 50 Hz stimulation for 5 s duration usually followed with post tetanic facilitation of transmission with non-depolarizing neuromuscular blockade drug rarely used by itself clinically clinically used with post tetanic count stimulation should not be given more frequently than every 6 minutes 100 Hz stimulation also available |
| Post tetanic count stimulation | usually used when large doses of non-depolarizing neuromuscular blockade drug have been administered, i.e., when there is no response to single-twitch or TOF stimulation the post tetanic count is the number of twitches before fadeaway when starting single-twitch stimulation at 1 Hz, 3 s after tetanic stimulation |
| Double burst stimulation | typically, two short bursts of 50 Hz tetanic stimulation separated by 750 ms. usually, each burst contains 3 pulses (20 ms) with a 1% duty cycle (0.2 ms). "fade" indicative of residual neuromuscular blockade is easier to feel clinically by tactile means than in TOF stimulation |

Typically, the electrical output of the nerve stimulator is a monophasic, rectangular (constant current; <55 mA) waveform in all modes of stimulation, each pulse lasting 0.25 ms with a rise time less than 20 microseconds. The time interval between the current pulses generated by the nerve stimulator is distinctive for each stimulation mode. The characteristics of the different nerve stimulation protocols are summarized in Table 1.

Clinically, the twitch response of the patient depends on whether the administered neuromuscular blockade drug is depolarizing (DNMBD, e.g., succinylcholine) or non-depolarizing (NNMBD, e.g., atracurium). Therefore, the simulation engine needs to know which kind of neuromuscular blockade drug is "used".

The twitch simulator also includes an electric pulse sensing means to detect the output from the nerve stimulator. Preferably, the sensing means is hidden from the view of the person being trained with the twitch simulator, such as within or underneath the hand of the manikin, to enhance the real-life atmosphere of the twitch simulator. This electric pulse sensing means must be able to differentiate between single-twitch, TOE and tetanic stimulation, thus also allowing post tetanic count stimulation. Preferably, the design of the sensing circuit should make it possible to identify DB stimulation. Furthermore, the electric pulse sensing means must be able to accept the signals coming from the twitch monitor for triggering an output device, such as a thumb twitch actuator. The circuit diagram for the preferred electric pulse sensing means is given in FIG. 2 but other sensing means can be constructed by one skilled in the art to accomplish the above requirements.

Figure 2:
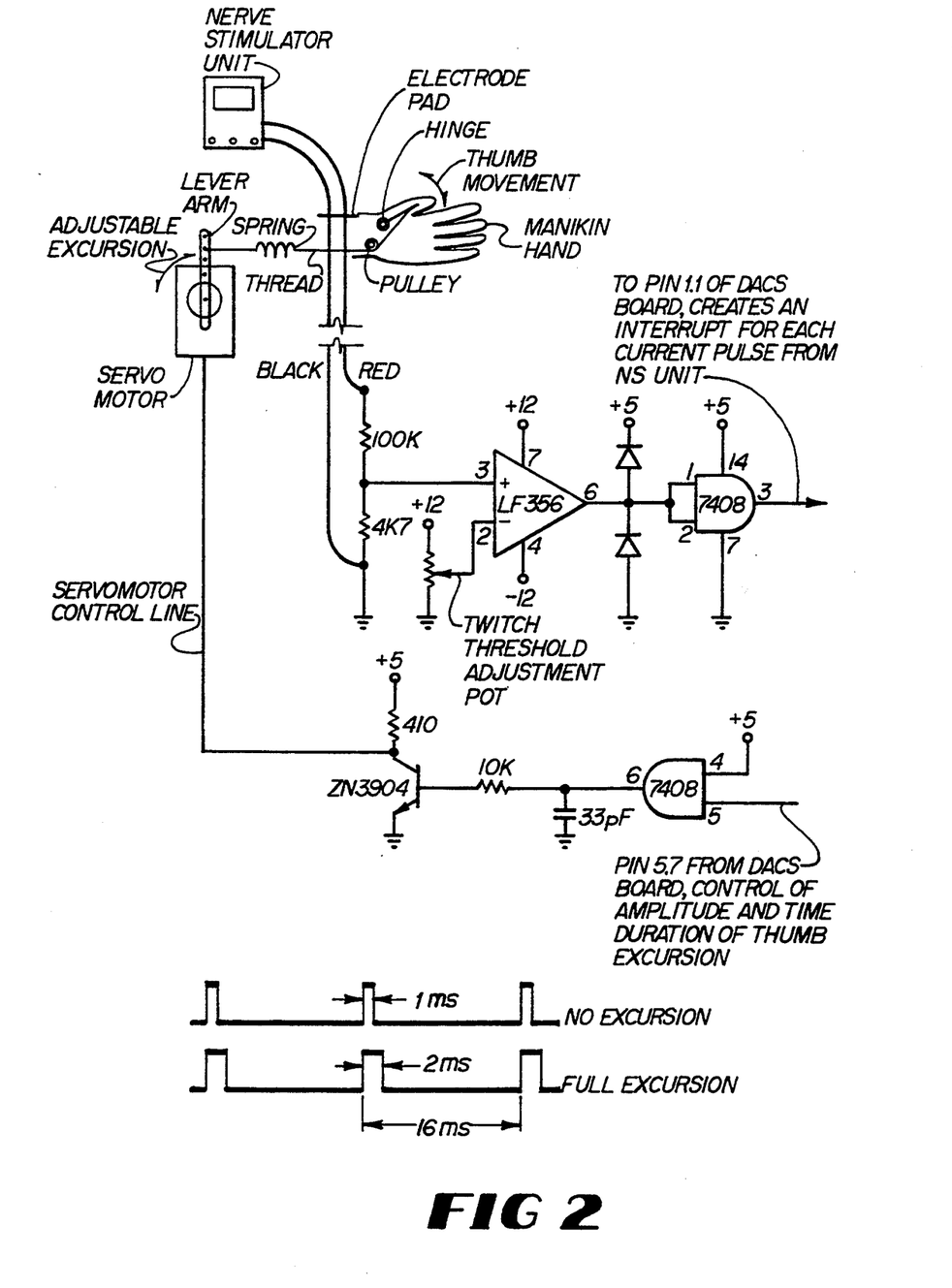
FIG. 2 shows the hardware and electronics of one embodiment of the twitch simulator according to the present invention.

Thus, typically, the electric pulse sensing means senses the current pulses delivered by the NS unit. There is a current control knob on the commercial NS unit that adjusts the magnitude of the current pulse. Thus, in the preferred embodiment, the current pulse magnitude can be adjusted from 0-55 mA by the trainee. As shown in FIG. 2, the square current pulse of 0.25 ms time duration creates a voltage pulse of the same duration at the ladder represented by the 100K and 4K7 resistors. The magnitude of the voltage pulse will be dependent on the current pulse magnitude set by the trainee according to $V=I/R$. The magnitude of the voltage pulse is compared to a threshold voltage set by the twitch threshold adjustment pot. If the magnitude of the voltage pulse is higher than the threshold voltage, an interrupt is created on pin 1.1 of the DACS board.

The detection of the mode of NS stimulation is done by measuring the time interval between current pulses, i.e., the time intervals between hardware interrupts generated on pin 1.1 of the DACS board. Thus, there are two components to the detection circuit: detection of the current pulse and measurement of the time interval between current pulses.

Preferably, the pulse sensing means also detects when the neuromuscular blockade drug is administered, how much of the neuromuscular blockade drug is administered, and the kind of neuromuscular blockade drug being used so as to differentiate between depolarizing and non-depolarizing neuromuscular blockade drugs. Alternatively, the kind of neuromuscular drug (non-depolarizing neuromuscular blockade drug or depolarizing neuromuscular blockade drug), the amount of drug injected and the exact point in time of injection can be entered by the instructor from a keyboard or touchscreen. For instance, the script for this scenario, e.g., induction of anesthesia, can be based on a finite state algorithm (FSA). As soon as the simulation engine computer has been instructed via the instructor input that a neuromuscular blockade drug has been injected, the FSA transitions to the next state and changes the degree of neuromuscular blockade from 0% to 100% in a gradual fashion that is specified in the hard-coded script.

The distributed processing network, which is described below, is an essential component of the twitch simulation. By distributing the processing details to various boards, such as DACS boards, information detected by the sensing circuitry in the input component of the simulator can be buffered for the simulation engine computer. Further, the distributed processing network is infinitely expandable. Preferably, the DACS board that controls the twitch simulator (DACS #3 of FIG. 4) is part of a distributed processing network which is controlled by the simulation engine computer. For instance, the simulation engine computer determines the degree of neuromuscular blockade and the type of neuromuscular blockade drug used and passes these values as the network variables 'BLOCKADE' and 'NMB_DRUG' addressed to the DACS #3 around the distributed processing network. These values are read by the software resident on the DACS #3 and are used to control the amplitude, time duration and pattern of the thumb excursion.

The twitch simulator also contains at least one output device, preferably a thumb twitch actuator. The thumb twitch actuator must provide a means of moving a manikin thumb in a fashion which is clinically realistic and thus, preferably, hidden from the sight of the trainer, such as in or below the hand of the manikin. The amplitude of the thumb movement should be adjustable so that fadeaway and different degrees of neuromuscular blockade can be displayed. Consequently, a proportional actuator that moves the thumb to different excursion amplitudes relative to the fingers on the hand was developed as described below.

A servomotor for radio controlled airplanes was used to provide the proportional actuation (Futaba FP-2GS, Futuba Corporation of America, Compton, Calif.). The degree of rotation of the servomotor was controlled by pulse width modulation of a signal with a cycle time of 16 ms. The pulse width is the time from the start of the 16 ms cycle during which the voltage is high at 6 V. The servomotor has no rotation for a pulse width of 1 ms and moves to full excursion for a pulse width of 2 ms. The clock frequency on the twitcher DACS was therefore increased to provide a minimum resolution of 0.1 ms. Thus, 11 discrete pulse widths ranging from 1.0 to 2.0 ms in steps of 0.1 ms could be generated and transmitted via pin 5.7 of the 80535 to modulate the thumb excursion according to 10 discrete amplitudes. Obviously, other means of proportionally moving the thumb are available and contemplated by the present invention.

The rotation of the servomotor was converted into a variable thumb excursion by mounting a lever arm of about 3 inches in length on the circular plate mounted on the servomotor output shaft. The lever arm had a series of holes drilled along its length to provide convenient and fast adjustment of the lever arm moment. The manikin hand was hollow and a hinged mechanism made of metal was inserted into the cavity in the thumb. The hinged part of the thumb was connected to the lever arm mounted on the servo motor via high strength surgical thread and three coil springs (in parallel) removed from ball point pens. The string was not connected in a direct straight line to the hinged part of the thumb because of the need to hide the string below the forearm. Pulleys were used to angle the pulling direction of the string to the desired orientation.

The purpose of the springs was to allow force transmission to the trainee's hand if tactile assessment of the degree of blockade is performed. The springs would not have been required if only visual assessment of the thumb twitch is performed. However anesthesiologists are taught to place their hand against the twitching thumb of the patient and gauge the degree of blockade by the force exerted by the patient's thumb on their hand. The springs thus allow force transmission to the trainee's hand while protecting the servomotor. In other words, if there were no springs, when the thumb is blocked from moving by the trainee's hand, the servomotor will try to reach the assigned position and will be prevented from doing so because there is no elasticity ("give") in the surgical thread. Consequently, a current overload on the servomotor can arise as the servomotor strains to reach the desired position but is prevented from doing so by the trainee's hand in contact with the simulated thumb. With the springs placed in line with the surgical thread, the servomotor can reach its assigned position even when the trainee's hand is blocking the excursion of the

TABLE 2

| Blockade Level | DEPOLARIZATION | | | NON-DEPOLARIZING | | |
|---|---|---|---|---|---|---|
| | Single Twitch | TOF | Tetanus | Single Twitch | TOF | Tetanus |
| 100% (totally paralyzed) | 0 | 0,0,0,0 | 0 | 0 | 0,0,0,0 | 0 |
| 90% | 2 | 2,2,2,2 | 1s 6 → 0 | 2 | 2,0,0,0 | 1s 6 → 0 |
| 80% | 4 | 4,4,4,4 | 1s 8 → 0 | 4 | 4,2,0,0 | 1s 8 → 0 |
| 70% | 6 | 6,6,6,6 | 1s 10 → 0 | 6 | 6,4,2,0 | 1s 10 → 0 |
| 60% | 8 | 8,8,8,8 | 2s 10 → 0 | 8 | 8,6,4,2 | 3s 10 → 0 |
| 50% | 10 | 10,10,10,10 | 3s 10 → 0 | 10 | 10,8,6,4 | 3s 10 → 0 | thumb. The springs arranged in parallel are extended and generate a force proportional to their extension past their equilibrium states, which is transmitted to the trainee's hand.

The thumb twitch actuator must be capable of modulating the twitch response, i.e., the variation of the amplitude, duration and pattern of the thumb excursion. Preferably, at least 10 discrete thumb excursion amplitudes are desired to allow the trainee to experience subtle but perceptibly different thumb excursions similar to the real-life situation. For instance, Table 2 depicts preferred thumb twitch actuator responses upon administration of different drugs and different nerve stimulation protocols. More preferably, a continuously variable thumb excursion capability is desired to simulate fade and degree of neuromuscular blockade. Further the thumb twitch actuator must move the thumb in apposition to the other four fingers of the manikin's hand to simulate a real hand.

As discussed above, the thumb twitch actuator should possess a means of sinking the current output of the twitch monitor. Preferably, the actuator also possesses means for increasing the skin resistance and decreasing the current transmission, to simulate, e.g., a patient that has become hypothermic and whose skin resistance is increasing. The script or mathematical model coded in the software sends a signal to the simulation engine that the patient is cold and the skin resistance should increase. The software then actuates an electronic switch that actually cuts in a higher resistance into the resistor ladder in FIG. 2 consisting of the 100K and 4K7 resistors in series. For example, a 200K resistor could be switched in via software to replace the 100K resistor. The sensing and actuating circuitry and hardware for one embodiment of the thumb twitch actuator are shown in FIG. 2.

The software and control requirements of the twitch simulator include the necessity for real time actuation of the thumb with no noticeable delay between the current pulse and thumb excursion. Further, the system must possess a timer counter to measure elapsed time from an event, e.g., end of tetanic stimulation. The control software must be able to differentiate between depolarizing and non-depolarizing neuromuscular blockade drugs and to move the thumb twitch actuator accordingly in combination with the degree of blockade and the identified mode of stimulation.

Preferably, the computer control system should provide for demonstration that the polarity of the NS electrode leads matters when one electrode is at the elbow and the other at the wrist, according to the results of J. Berger et al., *Anesthesiology*, 56:402 (1982). If the negative electrode is placed close to the ulnar nerve at the wrist and the positive electrode close to the ulnar nerve at the elbow, only the thumb twitches as when both leads are on the ulnar nerve at the wrist. If the negative electrode is used over the ulnar nerve at the elbow with the positive electrode at the wrist, the whole hand moves.

The preferred software makes use of the interrupt lines available on the DACS board, which is based on an 80535 chip, a member of the 8031/51 microcontroller family. Pin 1.1 of the 80535 microcontroller (IEX4) was used to detect each current pulse from the NS monitor. An interrupt was generated by the current pulse detection circuit whenever the NS unit transmitted a current pulse. The time interval between interrupts was measured. Because the time interval between current bursts or pulses is unique to each mode and sub-mode of nerve stimulation, the nerve stimulation protocol was readily identified as soon as the second current burst was detected.

Additionally, the computer control system can emulate various physiologic and NS monitor failure scenarios. For instance, a decreased thumb twitch mimicking muscle fatigue is portrayed if the computer control system detects that tetanic stimulation is being used more frequently than every 6 minutes. If tetanic stimulation is delivered too frequently (more than once every 4-6 minutes), the neuromuscular junction depletes its supply of the neurotransmitter, acetylcholine, faster than it can be re-synthesized. The result is an apparent "muscle fatigue". The twitch response to stimulation is not strong and characterized by fade which the unaware clinician incorrectly interprets as a relative overdose of the neuromuscular blocking drug. Thus, the clinician, or trainee, may incorrectly try to reverse the "neuromuscular blockade drug overdose" with "reversal" medications. All that is really needed is to wait for several minutes time for the acetylcholine stores to be re-synthesized.

Further, increasing the resistance of the skin causes a decrease in current transmission, which in turn leads to a decrease in the thumb twitch response to stimulation and may mislead the anesthesiologist about the level of neuromuscular blockade. Thus, the instant invention can provide a means for decreasing the current transmission to the electric pulse sensing means to simulate increasing skin resistance of the manikin. The current level display on the NS unit, such as Professional Instruments NS-2C, will cue the trainee to the fault.

NS unit low battery simulation can be indicated by a reduced excursion of the thumb and only 3 current pulses being delivered by the NS unit during TOF stimulation. Further, the control system can mimic the deep anesthesia obtained with halogenated agents, which is similar to administration of neuromuscular blockade drugs. Thus, if the simulation engine senses that an overdose of volatile halogenated anesthetics, such as halothane, enflurane, isoflurane or desflurane has been administered, it will simulate the neuromuscular blockade that accompanies a volatile anesthetic overdose.

Other effects, such as the effect that certain antibiotics have on neuromuscular blockade properties, the resistance of burn patients to neuromuscular blockade drugs, and the effect of diseases such as myasthenia that mimic neuromuscular blockade, can be suitably modeled by the control system. That is, a certain class of antibiotics (aminoglycosides) has side effects that mimic the action of neuromuscular blockade drugs. Therefore, if the simulation engine receives information that an antibiotic that belongs to that class has been administered in a dose sufficient to mimic neuromuscular blockade in that size of patient, the simulation engine alters the twitch of the thumb in a way that simulates the neuromuscular blockade effect of that class of antibiotics even though no neuromuscular blockade drug was injected into the patient. This will be confusing to the trainee but is an excellent way of teaching the side-effects of that class of antibiotics without experimenting on a real patient. Further, burn patients are known to be resistant to neuromuscular blockade drugs. Thus, in a simulation involving a burn patient, the twitch will not fade away, even when the simulation engine is informed via the sensors or the instructor that neuromuscular blockade drugs have been administered in a dose sufficient to induce neuromuscular blockade in that size of patient. Even in the presence of neuromuscular blockade agents, the thumb will keep on twitching as if no neuromuscular blockade was administered in simulated burn patients. In the case of Myasthenia, a disease of the nervous system, antibodies attack the receptors on the neuromuscular junction, thus simulating the effect of neuromuscular blockade drugs, i.e., they induce neuromuscular blockade. Thus, a simulation would involve a patient exhibiting neuromuscular blockade when stimulated with a NS unit even though (1) no neuromuscular blockade drug has been administered, (2) there is no volatile anesthetic overdose and (3) no antibiotic that mimics the action of neuromuscular blockade drugs has been administered.

Evoked Potentials Simulator

Evoked potentials are the electrical signals that travel along a nerve pathway (including its course through the spinal cord, brainstem, and into the cerebral cortex) in response to external stimulation. There are three types of evoked potentials currently monitored during different surgical procedures, each named according to the type of external stimulation: (1) somatosensory (SSEP), (2) auditory (AEP), and (3) visual (VEP). In each instance, the external stimulation and measured cortical evoked potentials are separated by the part of the central nervous system (e.g., spinal cord) at risk during a particular surgical procedure.

For example, during surgery on the spinal column (e.g., for scoliosis), SSEPs are used. Typically, nerves in the arms (i.e., median nerve) or legs (e.g., posterior tibial nerve) are stimulated with a nerve stimulation protocol comprising a square wave stimulus of 0.2-2.0 millisecond duration at rates from 1-2 Hz, and the small evoked potentials are measured from the cerebral cortex. Because the signals are very small (in the order of microvolts), complex signal averaging and summation algorithms are used by evoked potential monitors to measure and report the evoked potentials. If the surgeon retracts too hard on the spinal cord or disrupts the spinal cord blood supply by any other mechanism, the amplitude and latency of the evoked potentials will diminish or the EP will disappear altogether in seconds.

The rapid warning gives the surgical and anesthesia team time to correct or compensate for the problem before permanent damage results.

Similar approaches are used for AEP and VEP. Generally, AEPs are generated by delivering a nerve stimulation protocol comprising clicks of 100 milliseconds duration at 10 Hz through headphones into one ear of the patient and recording (again using signal averaging and summation) the evoked potentials over the cerebral cortex. An example of a clinical application of AEPs would be to monitor the integrity of the cranial nerve VIII during resection of a neuroma. Typically, VEPs are generated by delivering 3–5 millisecond flashes of light at 1–3 Hz by light emitting diodes housed in special goggles that fit over the closed eye or in special contact lenses. VEPs are recorded (using signal averaging and summation) over the occipital, parietal, and central scalp. VEPs are used when intracranial procedures put any portion of the visual system at risk, for example, the resection of pituitary tumors.

Figure 3:
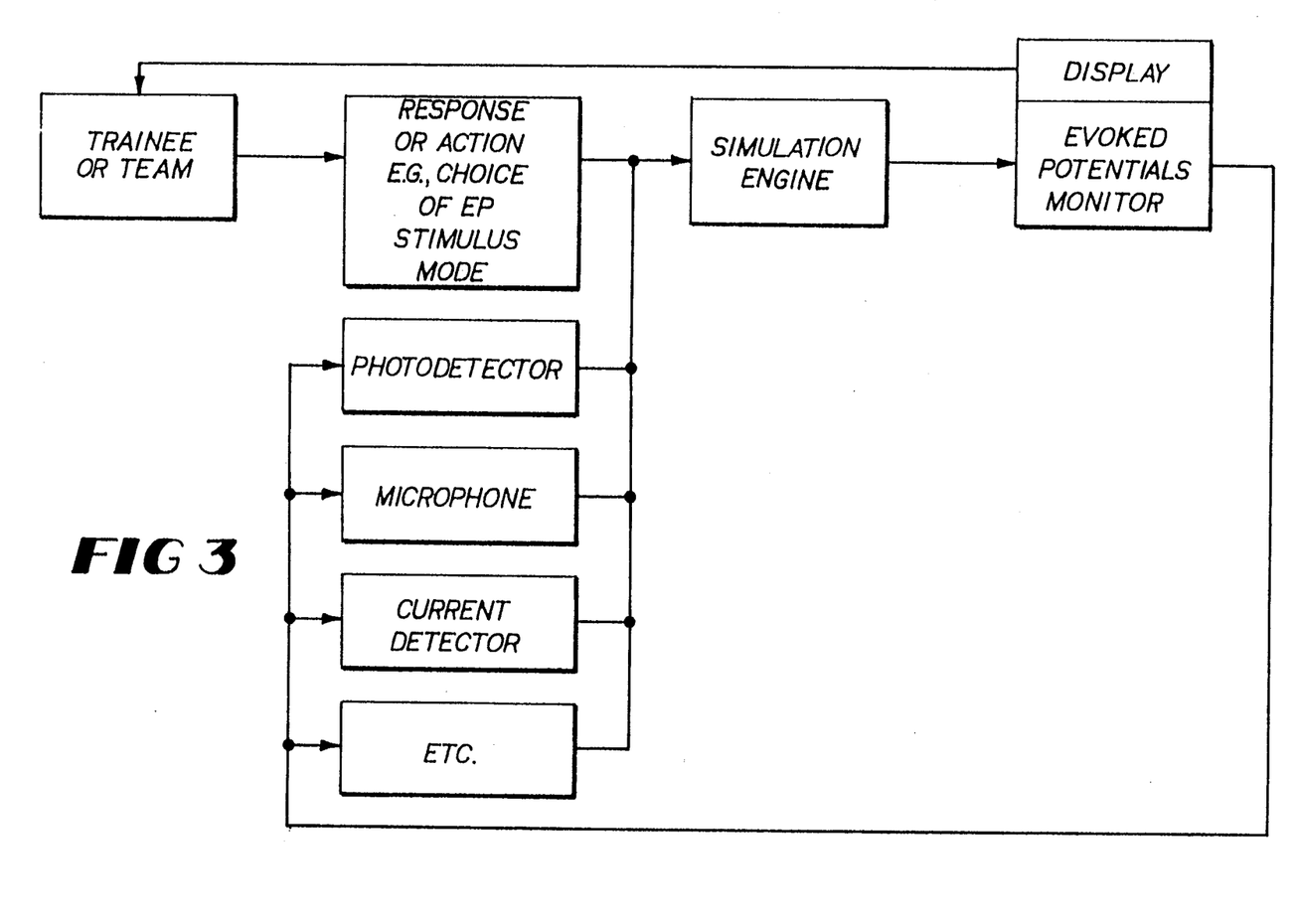
FIG. 3 shows a block diagram representation of the structure of one embodiment of the evoked potential simulator according to the present invention.

The EP simulator .electric pulse sensing means is similar to that of the twitch simulator. However, instead of detecting current pulses, a microphone can be used to detect the frequency and magnitude of sound pulses and a photodetector can be used to detect the frequency and intensity of light flashes as shown in FIG. 3.

As is apparent from the above discussion, the stimulation and recording of evoked potentials is exactly analogous to the stimulation and recording of the response to the twitch monitor (nerve stimulator). Though the routine clinical application of EPs is still in its infancy, several devices for intraoperative monitoring of EPs are commercially available. These instruments involve state of the art technology, and are more complex to operate than other monitoring instruments used by anesthesiologists. Further, the signals produced are more difficult to correctly interpret, because, in addition to surgical trespass resulting in damage to the nervous system, the anesthetics themselves and even the patient's temperature dramatically effect the EP signals. Complex medical equipment requiring complex interpretation lends itself well to training with a simulator.

Analogous to the neuromuscular blockade (twitch) simulator, the EP simulator resides as a software module housed on a DACS single board computer and electrode attachment sites are located on the patient mannequin. The electrode attachment sites include stimulation sites (e.g., median or posterior tibial nerves) and the sensing sites (e.g., over the scalp, neck and ears and eyes). Commands to and status information from the EP stimulator DACS is carried on the distributed processing network (DACS described below).

The EP simulator DACS waits until the stimulus from the EP monitor (electric current or voltage, sound, light) is detected, indicating that the EP monitor is beginning a measurement cycle. The EP simulator checks to make sure the stimulus was of the correct level and frequency to elicit the EP. If so, the EP simulation engine sends the appropriate EP to the sensing site electrode attachments.

Whether a normal or abnormal EP is portrayed depends on command messages from the Master DACS. For example, acute neurologic dysfunction resulting from excessive retraction may be directed by the FSA Control Software, and this message transmitted over the DACS network, with the EP simulator DACS responding by producing an abnormal EP. Other effects may be included in physiologic mathematical models running on the simulator's control computer. For example, a mathematical relationship between the alveolar concentration of anesthetic gas (or the blood concentration of an intravenous anesthetic) and the resulting EP may allow direct coupling of anesthetic dose and EP alterations due to anesthetics. Electrical and mechanical artifacts can be incorporated into the EP simulator in a manner exactly analogous to the neuromuscular blockade simulator.

An EP simulator is preferably based on the generic simulation structure depicted in FIG. 3. The stimuli delivered to the nerve being monitored is sensed by a circuit similar to the one used for the twitch simulator. In real time, the changes in the EP signals associated with the EP stimulus and the desired nerve condition or abnormality are generated by the simulation engine and projected to the user via the output component. The output component can be a real EP monitor, an EP monitor which has been modified to accept electrical signals from the simulation engine or a software emulation of an EP monitor running on a computer (see FIG. 3).

In response to delivery of anesthetics, the EP simulator introduces the typical disturbances in EP associated with anesthetics. Similarly, the disappearance of the EP associated with an accidental nick of the nerve by the surgeon's scalpel can be simulated.

Distributed Processing Network

There are several parallel yet linked processes continuously operating within a real patient. The distributed processing network according to the present invention provides this functionality for the manikin-associated processes.

Figure 4:
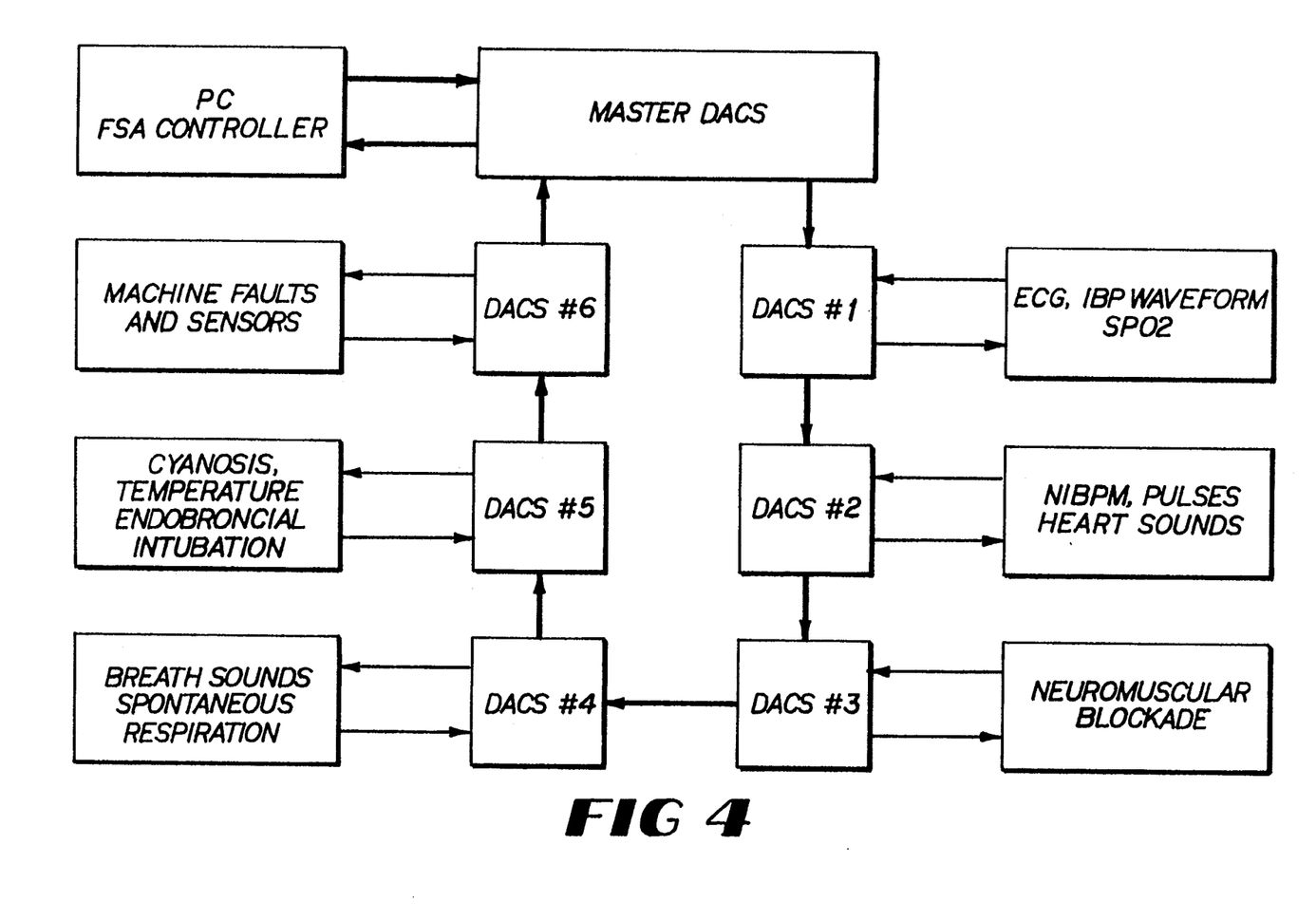
FIG. 4 shows a block diagram representation of one embodiment of the distributed processing network according to the present invention.
Figure 5:
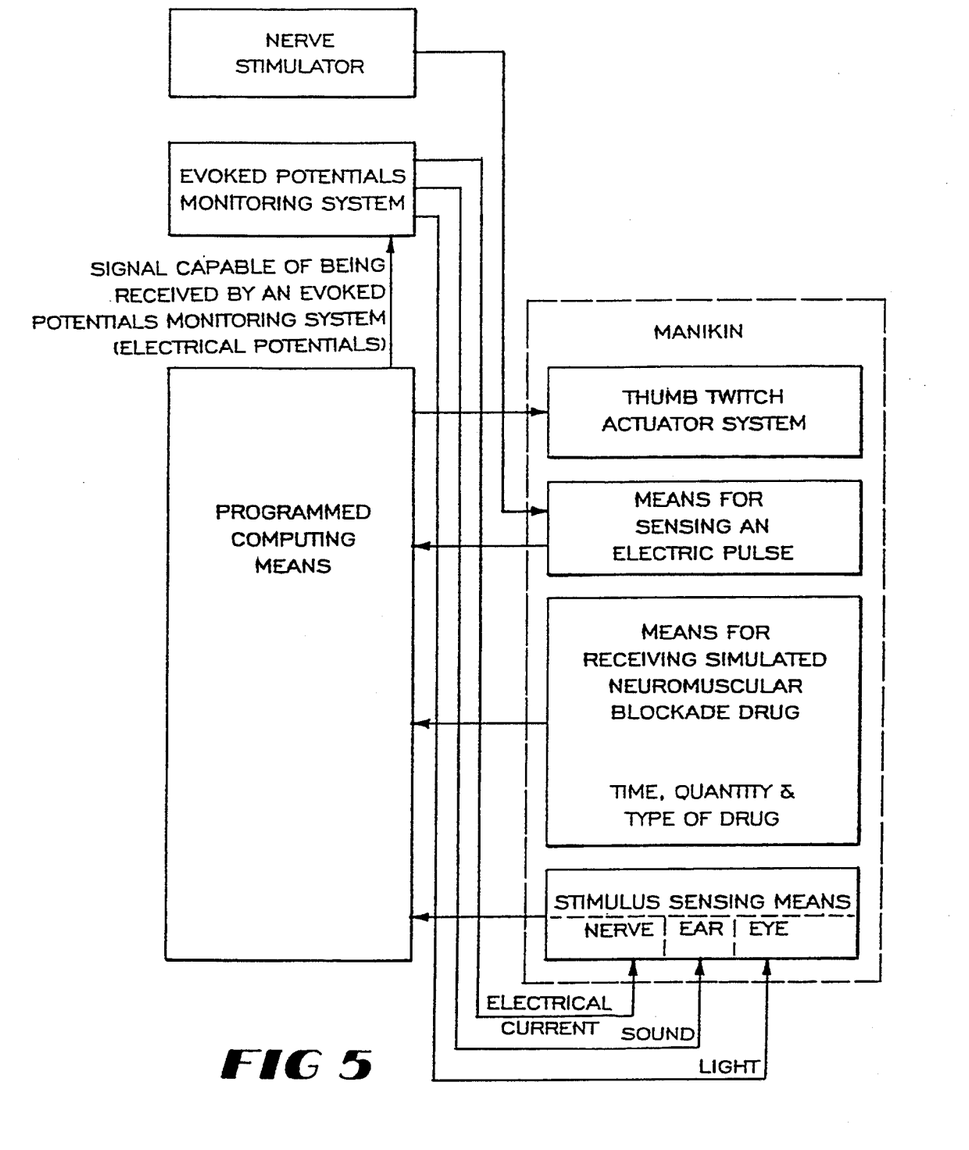
FIG. 5 shows a schematic diagram of the simulator of the invention.

FIG. 4 shows the preferred configuration of the distributed processing network for a general anesthesia simulator that incorporates the twitch simulator of the present invention, which consists of (1) a microcomputer (which runs the FSA Control Software) and (2) multiple DACS single-board computers arranged in a ring configuration network. The FSA Controller provides the DACS network with patient physiologic status information and fault actuation commands. The Controller also collects status information from the DACS network, i.e., inputs from the trainee (from the sensors) and instructor (from the instructor's console). Status information (events) received from the network dictate the course of events in the simulation.

The network uses a serial, RS-232 communications protocol. Messages fall into two categories: (1) commands to the simulator (a Command message) or (2) requests for status information (a Query message). Message flow is controlled through the Master DACS. The Master DACS has two responsibilities: (1) receive Commands from the FSA Control Software and relay them to the DACS Network; and (2) send Queries to the DACS Network to receive status information and relay this information to the FSA Control Software.

Command messages and Query messages are handled by the distributed processing network as follows. Command messages are initiated by the FSA Control Software. These messages are serially transmitted to the Master DACS. Each message is then passed on to the next DACS in the network. As messages arrive, each DACS board goes through the following process: (1) Is this a command message which is addressed to this DACS? If so, place this message in its incoming event queue; (2) Place the message just received in the DACS's outgoing event queue; (3) As quickly as possible, pass on all messages in the outgoing event queue to the next DACS in the network; and (4) In between incoming and outgoing messages, the DACS acts on the next message in its incoming event queue. For example, the DACS might be acting on a message to change the systolic blood pressure to 120 mm Hg.

Messages are passed sequentially from one DACS board to the next. As they arrive, each DACS goes through the aforementioned message processing algorithm. At some point, the Master DACS receives back the message it just sent out and the loop terminates.

As an example, a command from the FSA Control Software carries the instruction to change the patient's systolic blood pressure to 120 mm Hg. The Command message BP_SYS 120 would be passed from the FSA Control Software to the Master DACS. In turn, the Master DACS relays the information to the first DACS in the network. From FIG. 4, we see that DACS board #1 stimulates the monitor which reports Invasive Blood Pressure (IBP). As described, this message gets passed on to DACS board #2. This DACS, which controls pulsations in the mannequin arm from which the Noninvasive Blood Pressure (NIBP) monitor determines systolic blood pressure, acts on the instruction. Subsequent DACS receive this message and ignore the information since they are not concerned with blood pressure. The message successfully terminates when it is returned back to the Master DACS.

Unlike Command messages, Query messages are initiated by the Master DACS. In between receiving Command messages, the Master DACS will ask (query) the DACS network for status information. Again, as messages arrive, each DACS board goes through the following process: (1) Is this a Query message? If so, does this DACS have any status information to report?; (2) If this DACS does have status information to report, pass this information on to the next DACS in the network; and (3) If this DACS does not have status information to report, it passes the Query message on to the next DACS in the network.

Messages are passed sequentially from one DACS board to the next. As they arrive, each DACS goes through the aforementioned message processing algorithm. Eventually, the Master DACS receives a message back from the DACS network. Any returned status information is then reported to the FSA Control Software.

As an example, consider status information detected by the DACS network. Suppose the anesthesiologist changes the Tidal Volume Setting ($V_T$ Set) on the Mechanical Ventilator to 700 ml. This information is detected by DACS #6 in the network, which interfaces to the mechanical ventilator. When a Query message is received by DACS #6, the message is replaced with the status message (VT 700). This message is received by the Master DACS and relayed to the FSA Control Software.

In addition to serial information, the network hardware allows analog and digital signals to be transmitted in the DACS network. For example, a signal corresponding to the R wave of the electrocardiogram is transmitted along the network and used to synchronize pulses throughout the mannequin. This allows synchronization of ECG, blood pressure, palpable pulses, heart sounds, and optoplethysmogram. Each DACS board can selectively synchronize its own processes or ignore this information.

Software code for controlling a preferred embodiment of the instant twitch simulator follows.

Although the present method and apparatus have been described with reference to specific details of certain embodiments thereof, it is not intended that such details should be regarded as limitations upon the scope of the invention except as and to the extent that they are included in the accompanying claims.

```
/**
 * twitcher.c   v1.0 5/9/91 SL
 * The network interrupts cause the servomotor to jitter because the network
 * interrupt has a higher priority than the sysclk interrupt. The pulse width
 * modulation that controls the servomotor excursion amplitude is generated using
 * sysclk of timer 2.
 *
 * v2.0 5/28/91 SL;  sysclk-independent pwm using timer2 code by BP
 * sysclk-independent pwm using timer0 by RC
 * version 2.0 uses timer 0 to generate the pulse width modulation desired
 * irrespective of the sysclk interval chosen on timer 2.
 *
 * v3.0 7/14/91 SL; the tetanus response with non-depolarizing agents was
 * clinically incorrect in previous versions
 */ include <stdio.h>
include <text_io.h>
#include <stdlib.h>
#include <io515.h>
#include <os.h>
#include <netdefs.h>
include <var_list.h> define FIRST_PULSE      0    /* twitch monitor off or current level too low */
define TETANUS          1    /* No clinical difference between tetanus */
#define TOF              2    /* stimulation at 50 or 100 Hz, between TOF */
#define SINGLE_TWITCH    3    /* and TOF repeat, and between single twitch at */
                              /* 1 sec or 10 sec intervals */ define HIGH    P5.7 = 0      /* invert because of transistor driver */
define LOW     P5.7 = 1      /* 4/19/91 */ define RESTING    2000       /* 2 ms high time */
define FULL       1000       /* 1 ms high time */
#define PERIOD     16000      /* 16 ms cycle time */
define DURATION   20         /* default excursion duration: 20 16 ms cycles */ define NONE            0
define DEPOLARIZING    1
define NONDEPOLARIZING 2 data unsigned short int
    count,                /* count keeps track of the pulse number in TOF */
    mode,
    NMB_drug=NONE,
    block=NONE;           /* block is from 0 - 10; i.e., 0 - 100% blockade */
                          /* in increments of 10% */
data unsigned int
    interval,
    sysclk,
    tetanus_clk=0,
    excursion_duration=20,
    cycles;               /* cycles is the number of 16 ms cycles */
    pulseWidth=RESTING;   /* pulse width in microseconds */ data unsigned int period=16000;  /* period (microseconds) for pwm output */
data unsigned int cycle_time[2]; /* low, high */
data unsigned int duty_cycle=2000;

/*
 * void set_duty_cycle()
 *
 * This routine sets the duty cycle for the pwm output. The value of
 * high_time establishes the time (in microseconds) during which the
 * pwm output is high. It should be set to some value between 0 and
 * period.
 */
void set_duty_cycle(unsigned int high_time)
{
    cycle_time[1] = - high_time;
    cycle_time[0] = high_time - period;
} idata int timer0_reload = 0xFFFF;
    /* global variable to store timer 0 reload value */ void init_timer0(unsigned int period)
{
    timer0_reload = 0xFFFF - period + 1;
    TR0 = 0;                             /* disable timer 0 */
    ET0 = 0;                             /* Don't allow interrupts yet! */
    TH0 = timer0_reload >> 8;            /* Re-load timer 0 */
    TL0 = (char) timer0_reload;
    TMOD = TMOD | 0x01;

TF0 = 0;                             /* enable timer 0 as a 16-bit timer */
    TR0 = 1;                             /* clear timer 0 overflow flag */
    ET0 = 1;                             /* set to turn timer 1 on */
    EAL = 1;                             /* enable timer 0 interrupt */
                                         /* enable all interrupts */
} interrupt [0x0b] void timer_int()
{
    unsigned int timer_ticks;

if (high)
    {
        LOW;
        high = 0;
    }
    else
    {
        HIGH;
        high = 1;
        cycles++;
        if (cycles>excursion_duration) set_duty_cycle(RESTING);
    }
    timer_ticks = cycle_time[high];
    if (!timer_ticks)
        timer_ticks = cycle_time[high^1];

TH0 = (timer_ticks >> 8);
    TL0 = timer_ticks & 0xFF;
} interrupt [0x2b] void inc_sysclk()
{
    sysclk++;
    tetanus_clk++;
    TF2 = 0;    /* re-enable interrupt for sysclk */
} void sense_mode()
{
    if (interval < 7) mode = TETANUS;    /* changed from 1 to remove jitter */
    else                                  /* on Datascope display 7/14/91 SL */
```

```c
        if (interval < 11) mode = TOF;
        else
        if (interval < 21) mode = SINGLE_TWITCH;
        else
        {
            mode = FIRST_PULSE;
            excursion_duration = DURATION;
            tetanus_clk=0;
            count = 0;
        } unsigned short int
    TOF_table[11][3] = {   10,  11,  12,   /* 0% NM Blockade */
                           12,  13,  14,   /* 10% NM Blockade */
                           14,  15,  16,   /* 20% NM Blockade */
                           15,  16,  17,   /* 30% NM Blockade */
                           16,  17,  18,   /* 40% NM Blockade */
                           17,  18,  19,   /* 50% NM Blockade */
                           18,  19,  20,   /* 60% NM Blockade */
                           19,  20,  20,   /* 70% NM Blockade */
                           20,  20,  20,   /* 80% NM Blockade */
                           20,  20,  20,   /* 90% NM Blockade */
                           20,  20,  20 }; /* 100% NM Blockade */ unsigned short int
    depolarizing_tetanus_excursion_list[11] =
        {  10, 11, 12, 13, 14, 15, 16, 17, 18, 19, 20 };

unsigned short int
    depolarizing_tetanus_fade_list[11] =
        { 180, 150, 135, 120, 90, 75, 60, 45, 30, 15, 0 };

unsigned int
    nondep_tetanus_plateau_duration[11] =
        {  999,    /* 0% blockade; plateau for up to 50 seconds */
           999,    /* 10% blockade; plateau for up to 50 seconds */
                   /* because of interrupts on IEx4, sysclk does not keep real time;
                      therefore use a correction factor of 0.5 */
           40,     /* 20% blockade; 4 seconds plateau */
           35,     /* 30% blockade; 3.5 seconds plateau */
           30,     /* 40% blockade; 3 seconds plateau */
           25,     /* 50% blockade; 2.5 seconds plateau */
           20,     /* 60% blockade; 2 seconds plateau */
           15,     /* 70% blockade; 1.5 seconds plateau */
           10,     /* 80% blockade; 1 second plateau */
           7,      /* 90% blockade; 0.67 second plateau */
           3 };    /* 100% blockade; 0.33 second plateau */ void modulate_twitch_amplitude()
{
    if (NMB_drug==NONE)
    {
        set_duty_cycle(FULL);
        excursion_duration = DURATION;
    }
    else if (mode==FIRST_PULSE)
    {
        set_duty_cycle((10-block)*100);   /* RESTING-(10-block) */
        count = 0;
    }
    else if (NMB_drug == TETANUS)
    {
        if (NMB_drug == DEPOLARIZING)
        {
            set_duty_cycle(depolarizing_tetanus_excursion_list[block]*100);
            excursion_duration = depolarizing_tetanus_fade_list[block];
        }
        else   /* NONDEPOLARIZING DRUG */
        {
            if (tetanus_clk <= nondep_tetanus_plateau_duration[block])
            {
                if (block == 10) set_duty_cycle(1500);
                else
                {
                    set_duty_cycle(FULL);
                    excursion_duration = DURATION;  /* 0.32 s; 20 16 ms cycles */
                }
            }
            if ((tetanus_clk - nondep_tetanus_plateau_duration[block])
                < 10) set_duty_cycle(1350);
            else if ((tetanus_clk - nondep_tetanus_plateau_duration[block])
                < 20) set_duty_cycle(1400);
            else if ((tetanus_clk - nondep_tetanus_plateau_duration[block])
                < 30) set_duty_cycle(1525);
            else set_duty_cycle(RESTING);
        }
    }
    else if (mode==TOF)
    {
        if (NMB_drug==NONDEPOLARIZING)
        {
            set_duty_cycle(TOF_table[block][count]*100);
            count++;
        }
        else    /** DRUG = DEPOLARIZING **/
            set_duty_cycle((10-block)*100);
    }
    else if (mode==SINGLE_TWITCH) set_duty_cycle((10-block)*100);
}

/** Iex4_Interrupt() is triggered by each pulse from the twitch monitor.
 **/
Interrupt [0x5b] void Iex4_Interrupt()  /* enable positive transition activated
                                           interrupt on pin 1.1 */
{
    interval = sysclk;
    sense_mode();
    modulate_twitch_amplitude();
    sysclk = 0;
    cycles = 0;
}

/** enable_twitch_sync() enables the Iex4_Interrupt() handler
 **/
void enable_twitch_sync()
{
```

```c
P1.1 = 1;
EX4 = 1;            / Enable IEX4 Interrupt / void main()
{
    unsigned char event;
    int value;

IP0 = 0x24;     /** Give the network interrupt the highest priority, **/
    IP1 = 0x06;     / then timer 0, then timer 2 and last IEX4 interrupt / print_version();
    init_scc(NETWORK, BAUD_4800, 8, 'N', 1);
    var_used[DRUG] = TRUE;
    var_used[BLOCKADE] = TRUE;
    enable_network(ID_TWITCHER);
    puts("GAINESVILLE ANESTHESIA SIMULATOR");
    puts("           Version 1.999");
    puts("\n Neuro-Muscular Blockade DACS\n");

enable_twitch_sync();
    enable_sysclk(50000);   /* tick 20 times per second; 1 tick = 0.05s */ puts("initializing timer 0");
    init_timer0(50000);      /* first timer 0 interrupt in 50000 microseconds */
    set_duty_cycle(2000);    /** pwm output is high for 2000 microseconds i.e.,
                                 resting position **/
    puts("timer 0 initialized");
    puts ("period is fixed at 16 milliseconds");
    puts("Awaiting instructions from network");

for (;;)
    {
        if (sysclk>63000) sysclk=21;   /** to prevent incorrect mode sensing if
                                            interrupt occurs when sysclk happens
                                            to be less then 20
                                            Also, helps detect FIRST_PULSE **/
        if (tetanus_clk>63000) tetanus_clk=0;

if (event_ready())
        {
            /** Get the next event from the network;
            **/
            get_event(&event, &value);

if (event == BLOCKADE)
            {
                block=value;
                putstr("BLOCKADE = ");
                print_int(block);
                putchar('\n');
            }
            else if (event == DRUG)
            {
                NMB_drug=value;
                putstr("DRUG = ");
                print_int(NMB_drug);
                putchar('\n');
            }
            else if (event == EVENT_RESET)
            {
                block = 0;
                count=0;
                NMB_drug = NONE;
                puts("NMB_DACS Reset");
                send_event(EVENT_READY, ID_TWITCHER);
            }
```

What is claimed is:

1. A method of simulating ulnar nerve stimulation in real time in response to a simulated degree of neuromuscular blockade during simulated medical surgery using a manikin, comprising the steps of:
   (A) applying at least one electric pulse corresponding to a nerve stimulation protocol selected from the group consisting of single twitch, train of four, tetanic, post tetanic count and double burst, to a means for sensing an electric pulse associated with the manikin, wherein the at least one electric pulse is applied using a nerve stimulator;
   (B) detecting the at least one electric pulse and identifying the corresponding nerve stimulation protocol;
   (C) computing a simulated response to the identified nerve stimulation protocol and the simulated degree of neuromuscular blockade according to a time-and event-based script, a computer model or a combination of a time- and event-based script and a computer model; and
   (D) actuating at least one output device associated with the manikin in real time according to the computed simulated response to simulate the neuromuscular stimulation associated with the nerve stimulation protocol and the simulated degree of neuromuscular blockade, wherein the output device is a thumb twitch actuator which moves a thumb on a hand of the manikin relative to the fingers on the hand a distance, time duration and pattern computed according to the nerve stimulation protocol.

2. The method of claim 1, further comprising the steps of:
   (A) administering a simulated or real neuromuscular blockade drug to the manikin;
   (B) detecting the time at which the neuromuscular blockade drug is administered, detecting the quantity of neuromuscular blockade drug administered, and detecting the kind of neuromuscular blockade drug administered; and
   (C) utilizing the time the drug was administered, the quantity of drug administered, and the kind of drug administered in computing a simulated response on the manikin so as to provide a combined simulated response in accordance with both the degree of blockade and the identified nerve stimulation protocol.

3. A method of simulating ulnar nerve stimulation in real time in response to a simulated degree of neuromuscular blockade during simulated medical surgery using a manikin, comprising the steps of:
   (A) applying at least one electric pulse corresponding to a nerve stimulation protocol to a means for sensing an electric pulse associated with the manikin, wherein the at least one electric pulse is applied using a nerve stimulator;
   (B) detecting the at least one electric pulse and identifying the corresponding nerve stimulation protocol;
   (C) computing a simulated response to the identified nerve stimulation protocol and the simulated degree of neuromuscular blockade according to a time-and event-based script, a computer model or a combination of a time- and event-based script and a computer model; and
   (D) actuating at least one output device associated with the manikin in real time according to the computed simulated response to simlate the neuromuscular stimulation associated with the nerve stimulation protocol and the simulated degree of neuromuscular blockade, wherein the output device is a thumb twitch actuator which moves a thumb on a hand of the manikin relative to the fingers on the hand a distance, time duration and pattern computed according to the nerve stimulation protocol and the simulated degree of neuromuscular blockade, and wherein the thumb moves to one of at least 10 preset distances according to the calculated simulated response.

4. A method of simulating ulnar nerve stimulation in real time in response to a simulated degree of neuromuscular blockade during simulated medical surgery using a manikin, comprising the steps of:
   (A) applying at least one electric pulse corresponding to a nerve stimulation protocol to a means for sensing an electric pulse associated with the manikin, wherein the at least one electric pulse is applied using a nerve stimulator;
   (B) detecting the at least one electric pulse and identifying the corresponding nerve stimulation protocol;
   (C) computing a simulated response to the identified nerve stimulation protocol and the simulated degree of neuromusclar blockade according to a time-and event-based script, a computer model or a combination of a time- and event-based script and a computer model; and
   (D) actuating at least one output device associated with the manikin in real time according to the computed simulated response to simulate the neuromuscular stimulation associated with the nerve stimulation protocol and the simulated degree of neuromuscular blockade, wherein the output device is a thumb twitch actuator which moves a thumb on a hand of the manikin relative to the fingers on the hand a distance, time duration and pattern computed according to the nerve stimulation protocol and the simulated degree of neuromuscular blockade, and wherein the thumb is capable of transmitting a force related to the distance computed according to the nerve stimulation protocol and the simulated degree of neuromuscular blockade when movement of the thumb is impeded.

5. A method of simulating ulnar nerve stimulation in real time in response to a simulated degree of neuromuscular blockade during simulated medical surgery using a manikin, comprising the steps of:
   (A) applying at least one electric pulse corresponding to a nerve stimulation protocol to a means for sensing an electric pulse associated with the manikin, wherein the at least one electric pulse is applied using a nerve stimulator;
   (B) detecting at least one electric pulse and identifying the corresponding nerve stimulation protocol;
   (C) computing a simulated response to the identified nerve stimulation protocol and the simulated degree of neuromuscular blockade according to a time-and event-based script, a computer model or a combination of time- and event-based script and a computer model; and
   (D) actuating at least one output device associated with the manikin in real time according to the computed simulated response to simulate the neuromuscular stimulation associated with the nerve stimulation protocol and the simulated degree of neuromuscular blockade, wherein the output device is a thumb twitch actuator which moves a thumb on a hand of the manikin relative to the fingers on the hand distance, time duration and pattern computed according to the nerve stimulation protocol and the simulated degree of neuromuscular blockade, further comprising the step of simulating a low battery condition for the nerve stimulator by decreasing the distance the thumb moves according to the computed simulated response upon identification of a nerve stimulation protocol associated with a low battery condition.

6. A method of simulating nerve stimulation, wherein the simulated nerve stimulation is selected from the group consisting of electrical stimulation of the spinal cord or peripheral nerves, auditory stimulation of the cranial nerve and visual stimulation of the optical nerve according to a nerve stimulation protocol, in real time during simulated medical surgery using a manikin, comprising the steps of:

(A) applying at least one electric stimulus, auditory stimulus, or optical stimulus corresponding to a nerve stimulation protocol to a stimulus sensing means associated with the manikin, wherein the at least one electric stimulus, auditory stimulus, or optical stimulus is applied using an evoked potentials monitoring system;

(B) detecting the at least one electric stimulus, auditory stimulus, or optical stimulus and identifying the corresponding nerve stimulation protocol;

(C) computing a simulated response to the identified nerve stimulation protocol according to a time-and event-based script, a computer model or a combination of a time- and event-based script and a computer model; and (D) actuating at least one output device associated with the manikin in real time according to the computed simulated response to simulate the nerve stimulation associated with the nerve stimulation protocol, wherein the output device comprises a signal capable of being received by an evoked potentials monitoring system.

7. An apparatus for simulating ulnar nerve stimulation in response to a simulated degree of neuromuscular blockade during simulated medical surgery, comprising:

(A) a manikin;

(B) at least one output device associated with the manikin;

(C) means for sensing an electric pulse associated with the manikin, wherein the means for sensing an electric pulse is capable of detecting pulse frequency, pulse current and the time interval between electric pulses;

(D) means for applying at least one electric pulse corresponding to a nerve stimulation protocol to the means for sensing an electric pulse; and (E) programmed computing means associated wit the means for sensing an electric pulse for identifying the corresponding nerve stimulation protocol and for calculating a simulated response to the identified nerve stimulation protocol and the simulated degree of neuromuscular blockade and for actuating at least one output device associated with the manikin, wherein the output device is a thumb twitch actuator which moves a thumb on a hand of the manikin relative to the fingers on the hand a distance, time duration and pattern computed according to the nerve stimulation protocol and the simulated degree of neuromuscular blockade associated with the manikin, to simulate the neuromuscular stimulation in real time according to a time- and event-based script, a computer model or a combination of a time- and event-based script and a computer model.

8. The apparatus of claim 7, further comprising:

(A) means to the manikin for receiving a simulated or real neuromuscular blockade drug administered thereto;

(B) means for detecting the time at which the neuromuscular blockade drug is administered; for detecting the quantity of neuromuscular blockade drug administered; and for detecting the kind of neuromuscular blockade during administered; and (C) means associated with the programmed computing means for utilizing the time the drug was administered, the quantity of drug administered, and the kind of drug administered so as to provide a combined simulated response in accordance with both the degree of blockade and the identified nerve stimulation protocol.

9. The apparatus of claim 7, wherein the programmed computing means comprises a distributed processing network.

10. The apparatus of claim 7, wherein the means for applying at least one electric pulse is a nerve stimulator, and further comprising means for simulating a low battery condition for the nerve stimulator, wherein the stimulating means decreases the distance the thumb moves according to the computed simulated response upon identification of a nerve stimulation protocol associated with a low battery condition.

11. An apparatus for simulating ulnar nerve stimulation in response to a simulated degree of neuromuscular blockade during simulated medical surgery, comprising:

(A) a manikin;

(B) at least one output device associated with the manikin;

(C) means for sensing an electric pulse associated with the manikin, wherein the means for sensing an electric pulse is capable of detecting pulse frequency, pulse current and the time interval between electric pulses;

(D) means for applying at least one electric pulse corresponding to a nerve stimulation protocol to the means for sensing an electric pulse; and (E) programmed computing means associated with the means for sensing an electric pulse for identifying the corresponding nerve stimulation protocol and for calculating a simulated response to the identified nerve stimulation protocol and the simulated degree of neuromuscular blockade and for actuating at least one output device associated with the manikin, wherein the output device is a thumb twitch actuator which moves a thumb on a hand of the manikin relative to the fingers on the hand a distance, time duration and pattern computed according to the nerve stimulation protocol and the simulated degree of neuromuscular blockade associated with the manikin, to simulate the neuromuscular stimulation in real time according to a time- and event-based script, a computer model or a combination of a time- and event-based script and a computer model, and wherein the thumb twitch actuator moves the thumb to one of at least 10 preset distances according to the calculated simulated response.

12. An apparatus for simulating ulnar nerve neuromuscular stimulation in response to a simulated degree of neuromuscular blockade during simulated medical surgery, comprising:
  (A) a manikin;
  (B) at least one output device associated with the manikin;
  (C) means for sensing an electric pulse associated with the manikin, wherein the means for sensing an electric pulse is capable of detecting pulse frequency, pulse current and the time interval between electric pulses;
  (D) means for applying at least one electric pulse corresponding to a nerve stimulation protocol to the means for sensing an electric pulse; and
  (E) programmed computing means associated with the means for sensing an electric pulse for identifying the corresponding nerve stimulation protocol and for calculating a simulated response to the identified nerve stimulation protocol and the simulated degree of neuromuscular blockade and for actuating at least one output device associated with the manikin, wherein the output device is a thumb twitch actuator which moves a thumb on a hand of the manikin relative to the fingers on the hand a distance, time duration and pattern computed according to the nerve stimulation protocol and the simulated degree of neuromuscular blockade associated with the manikin, to simulate the neuromuscular stimulation in real time according to a time- and event-based script, a computer model or a combination of a time- and event-based script and a computer model, and wherein the thumb twitch actuator comprises means of transmitting a force related to the distance computed according to the nerve stimulation protocol and the simulated degree of neuromuscular blockade when movement of the thumb is impeded.

13. An apparatus for simulating nerve stimulation in response to a simulated degree of integrity of a nervous pathway, wherein the simulated nerve stimulation is selected from the group consisting of electrical stimulation of the spinal cord or peripheral nerves, auditory stimulation of the cranial nerve, and visual stimulation of the optical nerve to produce simulated evoked potentials, during simulated medical surgery, comprising:
  (A) a manikin;
  (B) at least one output device associated with the manikin;
  (C) means for sensing a stimulus associated with the manikin, wherein the means for sensing a stimulus is capable of detecting stimulus frequency, stimulus magnitude, stimulus pattern and the time interval between stimuli;
  (D) means for applying at least one electric stimulus, auditory stimulus, or optical stimulus corresponding to a nerve stimulation protocol to the means for sensing a stimulus; and
  (E) programmed computing means associated with the means for sensing a stimulus for identifying the corresponding nerve stimulation protocol and for calculating a simulated response to the identified nerve stimulation protocol and the simulated degree of integrity of the nervous pathway being monitored and for actuating at least one output device associated with the manikin to simulate the nerve stimulation in real time according to a time- and event-based script, a computer model or a combination of a time- and event-based script and a computer model, wherein the output device comprises a signal capable of being received by an evoked potentials monitoring system.

14. An anesthesiological training simulator capable of simulating ulnar nerve stimulation in response to a simulated degree of neuromuscular blockade, wherein the simulator comprises a manikin and is capable of simulating spontaneous breathing, controlled mechanical ventilation, breath sounds, heart tones, and palpable radial and carotid artery pulses, comprising:
  (A) means for sensing an electric pulse associated with the manikin, wherein the means for sensing an electric pulse is capable of detecting pulse frequency, pulse current and the time interval between electric pulses;
  (B) at least one output device associated with the manikin, wherein the at least one output device is selected from the group consisting of a thumb twitch actuator and a means for decreasing the current transmission to the means for sensing an electric pulse to simulate increasing skin resistance of the manikin, and wherein said thumb twitch actuator moves a thumb on a hand of the manikin relative to the fingers on the hand a distance, time duration and pattern computed according to the nerve stimulation protocol and the simulated degree of neuromuscular blockade associated with the manikin;
  (C) means for applying at least one electric pulse corresponding to a nerve stimulation protocol to the means for sensing an electric pulse; and
  (D) programmed computing means associated with the means for sensing an electric pulse for identifying the corresponding nerve stimulation protocol and for calculating a simulated response to the identified nerve stimulation protocol and the simulated degree of neuromuscular blockade and for actuating at least one output device associated with the manikin to simulate the neuromuscular stimulation in real time according to a time and event-based script, a computer model or a combination of a time and event-based script and a computer model.

15. A method of simulating nerve stimulation in real time in response to a simulated degree of integrity of a nervous pathway during simulated medical surgery using a manikin, comprising the steps of:
  (A) applying, according to a nerve stimulation protocol, at least one stimulus selected from the group consisting of electrical stimulation of the spinal cord or peripheral nerves, auditory stimulation of the cranial nerve and visual stimulation of the optical nerve to produce simulated evoked potentials, to a means for sensing a stimulus associated with the manikin, wherein the at least one stimulus is applied using an evoked potentials monitoring system;
  (B) detecting the at least one stimulus and identifying the corresponding nerve stimulation protocol;
  (C) computing a simulated response to the identified nerve stimulation protocol and the simulated degree of integrity of the nervous pathway being monitored according to a time- and event-based script, a computer model or a combination of a time- and event-based script and a computer model; and (D) actuating at least one output device associated with the manikin in real time according to the computed simulated response to simulate the nerve stimulation associated with the nerve stimulation protocol and the simulated degree of integrity of the nervous pathway being monitored, wherein the output device comprises a signal capable of being received by an evoked potentials monitoring system.

16. A method of simulating ulnar nerve stimulation in real time in response to a simulated degree of neuromuscular blockade during simulated medical surgery using a manikin, comprising the steps of:

(A) applying at least one electric pulse corresponding to a nerve stimulation protocol selected from the group consisting of single twitch, train of four, tetanic, post tetanic count and double burst, to a means for sensing an electric pulse associated with the manikin, wherein the at least one electric pulse is applied using a nerve stimulator;

(B) detecting the at least one electric pulse and identifying the corresponding nerve stimulation protocol;

(C) computing a simulated response to the identified nerve stimulation protocol and the simulated degree of neuromuscular blockade according to a time- and event-based script, a computer model or a combination of a time- and event-based script and a computer model; and (D) actuating at least one output device associated with the manikin in real time according to the computed simulated response to simulate the neuromuscular stimulation associated with the nerve stimulation protocol and the simulated degree of neuromuscular blockade, wherein the output device comprises a means for decreasing the current transmission to the means for sensing an electric pulse to simulate increasing skin resistance of the manikin.

17. An apparatus for simulating ulnar nerve stimulation in response to a simulated degree of neuromuscular blockade during simulated medical surgery, comprising:

(A) a manikin;
(B) at least one output device associated with the manikin;
(C) means for sensing an electric pulse associated with the manikin, wherein the means for sensing an electric pulse is capable of detecting pulse frequency, pulse current and the time interval between electric pulses;
(D) means for applying at least one electric pulse corresponding to a nerve stimulation protocol to the means for sensing an electric pulse; and
(E) programmed computing means associated with the means for sensing an electric pulse for identifying the corresponding nerve stimulation protocol and for calculating a simulated response to the identified nerve stimulation protocol and the simulated degree of neuromuscular blockade and for actuating at least one output device associated with the manikin, wherein the output device comprises a means for decreasing the current transmission to the means for sensing an electric pulse to simulate increasing skin resistance of the manikin, to simulate the neuromuscular stimulation in real time according to a time- and event-based script, a computer model or a combination of a time- and event-based script and a computer model.

18. An apparatus for simulating nerve stimulation in response to a simulated degree of integrity of a nervous pathway during simulated medical surgery, wherein the simulated nerve stimulation is selected from the group consisting of electrical stimulation of the spinal cord or peripheral nerves, auditory stimulation of the cranial nerve, and visual stimulation of the optical nerve to produce simulated evoked potentials, comprising:

(A) a manikin;
(B) at least one output device associated with the manikin, wherein the at least one output device comprises a signal capable of being received by an evoked potentials monitoring system;
(C) means for sensing a stimulus associated with the manikin, wherein the means for sensing a stimulus is capable of detecting stimulus frequency, stimulus magnitude, stimulus pattern and the time interval between stimuli;
(D) means for applying at least one electric stimulus, auditory stimulus, or optical stimulus corresponding to a nerve stimulation protocol to the means for sensing a stimulus; and
(E) programmed computing means associated with the means for sensing a stimulus for identifying the corresponding nerve stimulation protocol and for calculating a simulated response to the identified nerve stimulation protocol and the simulated degree of integrity of the nervous pathway being monitored and for actuating at least one output device associated with the manikin to simulate the nerve stimulation in real time according to a time- and event-based script, a computer model or a combination of a time- and event-based script and a computer model.

19. The method of claim 1, wherein the thumb moves to one of at least 10 preset distances according to the calculated simulated response.

20. The method of claim 1, wherein the thumb is capable of transmitting a force related to the distance computed according to the nerve stimulation protocol when movement of the thumb is impeded.

21. The method of claim 1, further comprising the step of simulating a low battery condition for the nerve stimulator by decreasing the distance the thumb moves according to the computed simulated response upon identification of a nerve stimulation protocol associated with a low battery condition.

22. The apparatus of claim 7, wherein the thumb twitch actuator moves the thumb to one of at least 10 preset distances according to the calculated simulated response.

23. The apparatus of claim 7, wherein the thumb twitch actuator comprises means of transmitting a force related to the distance computed according to the nerve stimulation protocol when movement of the thumb is impeded.

* * * * *